United States Patent
Scofield et al.

(10) Patent No.: US 11,292,476 B2
(45) Date of Patent: Apr. 5, 2022

(54) PERSONALIZATION OF AUTOMATED VEHICLE CONTROL

(71) Applicant: INRIX INC., Kirkland, WA (US)

(72) Inventors: Christopher L. Scofield, Seattle, WA (US); Scott Sedlik, Mercer Island, WA (US)

(73) Assignee: INRIX Inc., Kirkland, WA (US)

(*) Notice: Subject to any disclaimer, the term of this patent is extended or adjusted under 35 U.S.C. 154(b) by 312 days.

(21) Appl. No.: 15/121,123

(22) PCT Filed: Mar. 3, 2015

(86) PCT No.: PCT/US2015/018379
§ 371 (c)(1),
(2) Date: Aug. 24, 2016

(87) PCT Pub. No.: WO2015/134417
PCT Pub. Date: Sep. 11, 2015

(65) Prior Publication Data
US 2017/0015318 A1   Jan. 19, 2017

Related U.S. Application Data

(60) Provisional application No. 61/946,962, filed on Mar. 3, 2014.

(51) Int. Cl.
*G05D 1/00* (2006.01)
*B60W 40/04* (2006.01)
(Continued)

(52) U.S. Cl.
CPC ......... *B60W 40/04* (2013.01); *A61B 5/02055* (2013.01); *A61B 5/369* (2021.01);
(Continued)

(58) Field of Classification Search
CPC .......... G08G 1/096791; G08G 1/0967; G08G 1/096822; G08G 1/012; G08G 1/0962;
(Continued)

(56) References Cited

U.S. PATENT DOCUMENTS 6,553,301 B1* 4/2003 Chhaya .................. B60K 6/54
701/54
6,836,719 B2 12/2004 Andersson et al.
(Continued)

FOREIGN PATENT DOCUMENTS

DE        19843395 A1    3/2000
EP        0952428 A     10/1999
(Continued)

OTHER PUBLICATIONS

Corresponding International Application No. PCT/US2015/018379, International Search report and written opinion dated Jul. 1, 2015.
(Continued)

*Primary Examiner* — Gennam M Mott
(74) *Attorney, Agent, or Firm* — Cooper Legal Group, LLC

(57) ABSTRACT

Vehicles feature various forms of automated driving control, such as speed control and braking distance monitoring. However, the parameters of automated control may conflict with the user driving behaviors of the user; e.g., braking distance maintained with respect to a leading vehicle may seem overcautious to users who prefer shorter braking distances, and unsafe to users who prefer longer braking distances. Presented herein are techniques for controlling vehicles according to the user driving behaviors of users. While a user operates a vehicle in a driving context, a device monitors various driving features (e.g., acceleration or braking) to determine various user driving behaviors. When requested to control a driving feature of the vehicle, a
(Continued)

controller may identify the user driving behaviors of the user in the driving context, and control the driving features according to the user driving behaviors, thus personalizing automated driving to the preferences of the user.

20 Claims, 9 Drawing Sheets

(51) Int. Cl.
| | |
|---|---|
| H04W 4/50 | (2018.01) |
| G06N 20/00 | (2019.01) |
| G06F 16/29 | (2019.01) |
| H04W 4/024 | (2018.01) |
| H04W 4/029 | (2018.01) |
| G08G 1/01 | (2006.01) |
| B60W 40/08 | (2012.01) |
| B60W 40/09 | (2012.01) |
| G08G 1/09 | (2006.01) |
| G08G 1/0967 | (2006.01) |
| G07B 15/06 | (2011.01) |
| G08G 1/0968 | (2006.01) |
| G08G 1/097 | (2006.01) |
| H04W 12/08 | (2021.01) |
| A61B 5/369 | (2021.01) |
| B60W 30/14 | (2006.01) |
| G07C 5/00 | (2006.01) |
| A61B 5/0205 | (2006.01) |
| A61B 5/00 | (2006.01) |
| G05D 1/02 | (2020.01) |
| H04B 1/3822 | (2015.01) |
| H04L 67/02 | (2022.01) |
| H04L 67/306 | (2022.01) |
| B64C 39/02 | (2006.01) |
| H04B 7/185 | (2006.01) |
| G06Q 20/10 | (2012.01) |
| G06Q 30/02 | (2012.01) |
| H04M 15/00 | (2006.01) |
| G06Q 40/08 | (2012.01) |
| H04L 9/32 | (2006.01) |
| B60R 16/023 | (2006.01) |
| G07B 15/00 | (2011.01) |
| G08G 1/065 | (2006.01) |
| G01C 21/36 | (2006.01) |
| H04W 4/42 | (2018.01) |
| H04W 4/40 | (2018.01) |
| G01C 21/34 | (2006.01) |
| G08G 1/07 | (2006.01) |
| G08G 1/0962 | (2006.01) |
| G08G 1/0965 | (2006.01) |
| H04W 4/48 | (2018.01) |
| A61B 5/024 | (2006.01) |
| A61B 5/0531 | (2021.01) |
| G06Q 50/30 | (2012.01) |

(52) U.S. Cl.
CPC ........ *A61B 5/4845* (2013.01); *B60R 16/0236* (2013.01); *B60W 30/143* (2013.01); *B60W 40/08* (2013.01); *B60W 40/09* (2013.01); *B64C 39/024* (2013.01); *G01C 21/3415* (2013.01); *G01C 21/3469* (2013.01); *G01C 21/3617* (2013.01); *G01C 21/3655* (2013.01); *G01C 21/3667* (2013.01); *G01C 21/3682* (2013.01); *G05D 1/0011* (2013.01); *G05D 1/0088* (2013.01); *G05D 1/021* (2013.01); *G06F 16/29* (2019.01); *G06N 20/00* (2019.01); *G06Q 20/102* (2013.01); *G06Q 30/0283* (2013.01); *G06Q 40/08* (2013.01); *G07B 15/00* (2013.01); *G07B 15/063* (2013.01); *G07C 5/008* (2013.01); *G08G 1/012* (2013.01); *G08G 1/0112* (2013.01); *G08G 1/0129* (2013.01); *G08G 1/0141* (2013.01); *G08G 1/0145* (2013.01); *G08G 1/065* (2013.01); *G08G 1/07* (2013.01); *G08G 1/093* (2013.01); *G08G 1/097* (2013.01); *G08G 1/0962* (2013.01); *G08G 1/0965* (2013.01); *G08G 1/0967* (2013.01); *G08G 1/096725* (2013.01); *G08G 1/096741* (2013.01); *G08G 1/096775* (2013.01); *G08G 1/096791* (2013.01); *G08G 1/096811* (2013.01); *G08G 1/096822* (2013.01); *G08G 1/096838* (2013.01); *H04B 1/3822* (2013.01); *H04B 7/18504* (2013.01); *H04L 9/3247* (2013.01); *H04L 67/02* (2013.01); *H04L 67/306* (2013.01); *H04M 15/60* (2013.01); *H04W 4/024* (2018.02); *H04W 4/029* (2018.02); *H04W 4/40* (2018.02); *H04W 4/42* (2018.02); *H04W 4/50* (2018.02); *H04W 12/08* (2013.01); *A61B 5/024* (2013.01); *A61B 5/0531* (2013.01); *B60W 2040/0809* (2013.01); *B60W 2040/0872* (2013.01); *B60W 2540/22* (2013.01); *B60W 2552/00* (2020.02); *B60W 2555/20* (2020.02); *B60W 2710/1044* (2013.01); *B60W 2710/18* (2013.01); *B60W 2720/10* (2013.01); *B64C 2201/123* (2013.01); *G01C 21/3608* (2013.01); *G06Q 50/30* (2013.01); *G06Q 2240/00* (2013.01); *H04W 4/48* (2018.02)

(58) Field of Classification Search
CPC ...... G08G 1/07; G08G 1/0141; G08G 1/0129; G08G 1/0112; G08G 1/096838; G08G 1/0965; G08G 1/065; G08G 1/096811; G08G 1/0145; G08G 1/097; G07B 15/00; G01C 21/3469; G01C 21/3415; B60R 16/0236; H04L 67/306; H04L 9/3247; H04L 67/02; H04M 15/60; G06Q 30/0283; G06Q 20/102; G06Q 40/08; G06Q 2240/00; G06Q 50/30; G06F 17/30241; H04W 12/08; H04W 4/046; H04W 4/48; H04W 4/50; A61B 5/0476; A61B 5/0531; A61B 5/024; A61B 5/02055; A61B 5/4845; G05D 1/0011; G05D 1/0088; G05D 1/021; H04B 7/18504; H04B 1/3822; G07C 5/008; B60W 2710/1044; B60W 2710/18; B60W 2720/10; B60W 30/143; G06N 99/005; B64C 2201/123; B64C 39/024
See application file for complete search history.

(56) References Cited

U.S. PATENT DOCUMENTS

| | | | |
|---|---|---|---|
| 9,381,916 B1* | 7/2016 | Zhu ...................... | G01S 17/931 |
| 2001/0033235 A1 | 10/2001 | Shinada | |
| 2006/0208169 A1 | 9/2006 | Breed | |
| 2007/0124027 A1 | 5/2007 | Betzitza et al. | |
| 2010/0070163 A1 | 3/2010 | Liu et al. | |
| 2011/0224893 A1* | 9/2011 | Scofield ............ | G01C 21/3492 |
| | | | 701/119 |
| 2011/0251734 A1 | 10/2011 | Schepp et al. | |
| 2012/0078496 A1* | 3/2012 | Lindhuber ............ | B60K 35/00 |
| | | | 701/123 |

(56) References Cited

U.S. PATENT DOCUMENTS

| | | |
|---|---|---|
| 2012/0083960 A1 | 4/2012 | Zhu et al. |
| 2012/0109508 A1 | 5/2012 | Rothschild |
| 2012/0226421 A1 | 9/2012 | Kote et al. |
| 2012/0316699 A1 | 12/2012 | Filev et al. |
| 2013/0096818 A1* | 4/2013 | Vicharelli .......... G01C 21/3469 701/423 |
| 2013/0204455 A1 | 8/2013 | Chia et al. |
| 2013/0218427 A1* | 8/2013 | Mukhopadhyay .... B60W 40/09 701/51 |
| 2014/0081573 A1* | 3/2014 | Urmson ................ G01W 1/10 702/3 |
| 2014/0371981 A1* | 12/2014 | Nordbruch ......... G06K 9/00845 701/36 |
| 2015/0035666 A1* | 2/2015 | Scofield .............. G08G 1/0112 340/439 |
| 2015/0039215 A1* | 2/2015 | Wu .................... G01C 21/3469 701/123 |
| 2015/0046197 A1* | 2/2015 | Peng ...................... G01W 1/00 705/4 |
| 2015/0158486 A1* | 6/2015 | Healey ................ B60W 30/12 701/23 |
| 2015/0258996 A1* | 9/2015 | Victor ................ G08G 1/0962 340/576 |

FOREIGN PATENT DOCUMENTS

| | | |
|---|---|---|
| EP | 1302356 A1 | 4/2003 |
| EP | 1901053 A | 3/2008 |

OTHER PUBLICATIONS

EP Search Report cited in EP Application No. 15757978.0 dated Dec. 1, 2017, 9 pgs.

Corresponding European Patent Application No. 1575978.0, Summons to attend oral proceedings pursuant to Rule 115(1) EPC, dated Aug. 6, 2021.

* cited by examiner

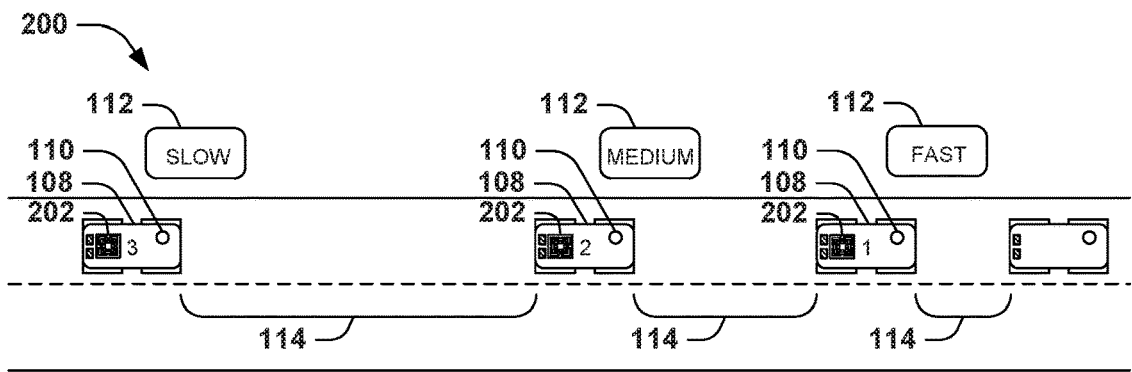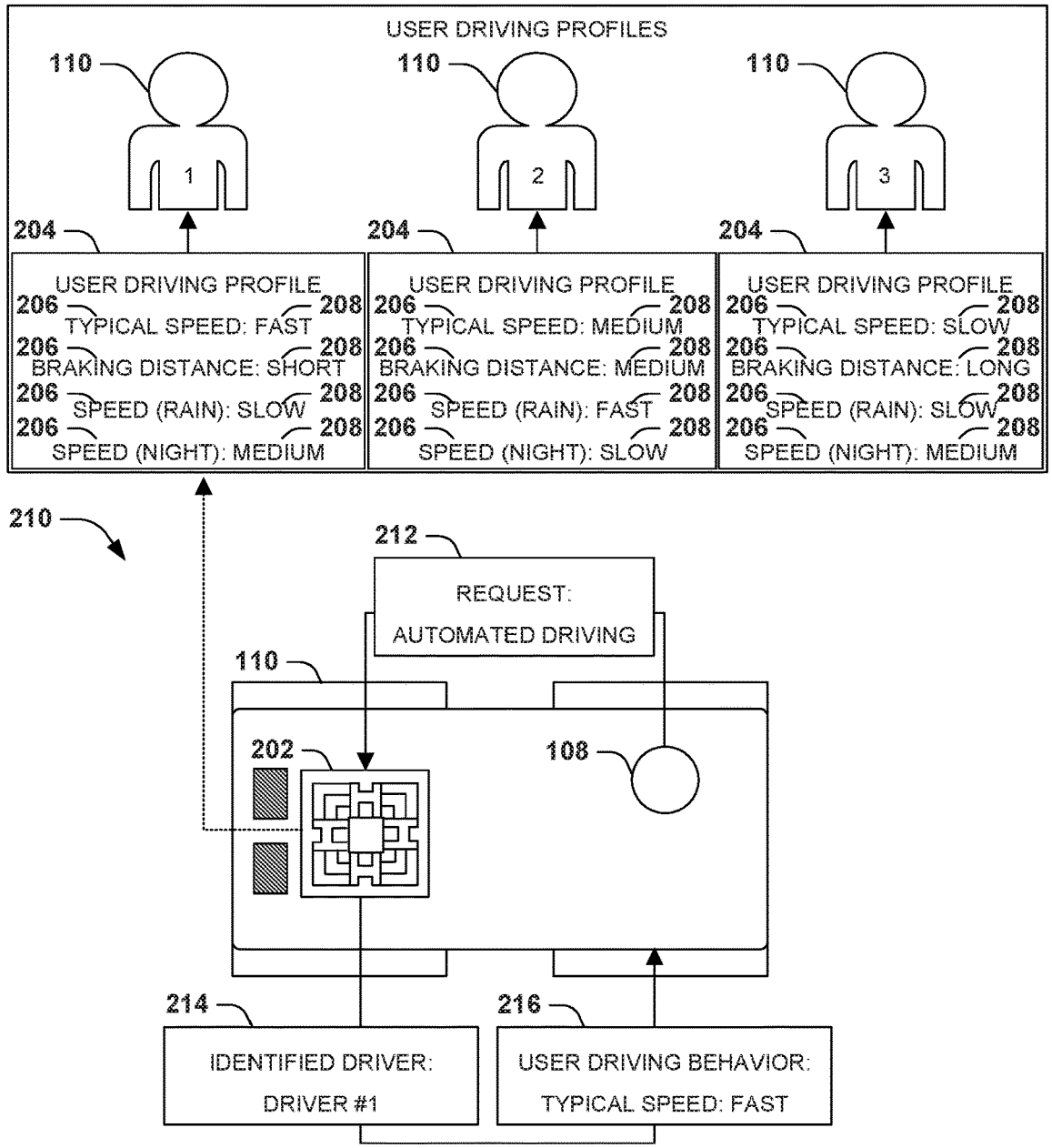
FIG. 2

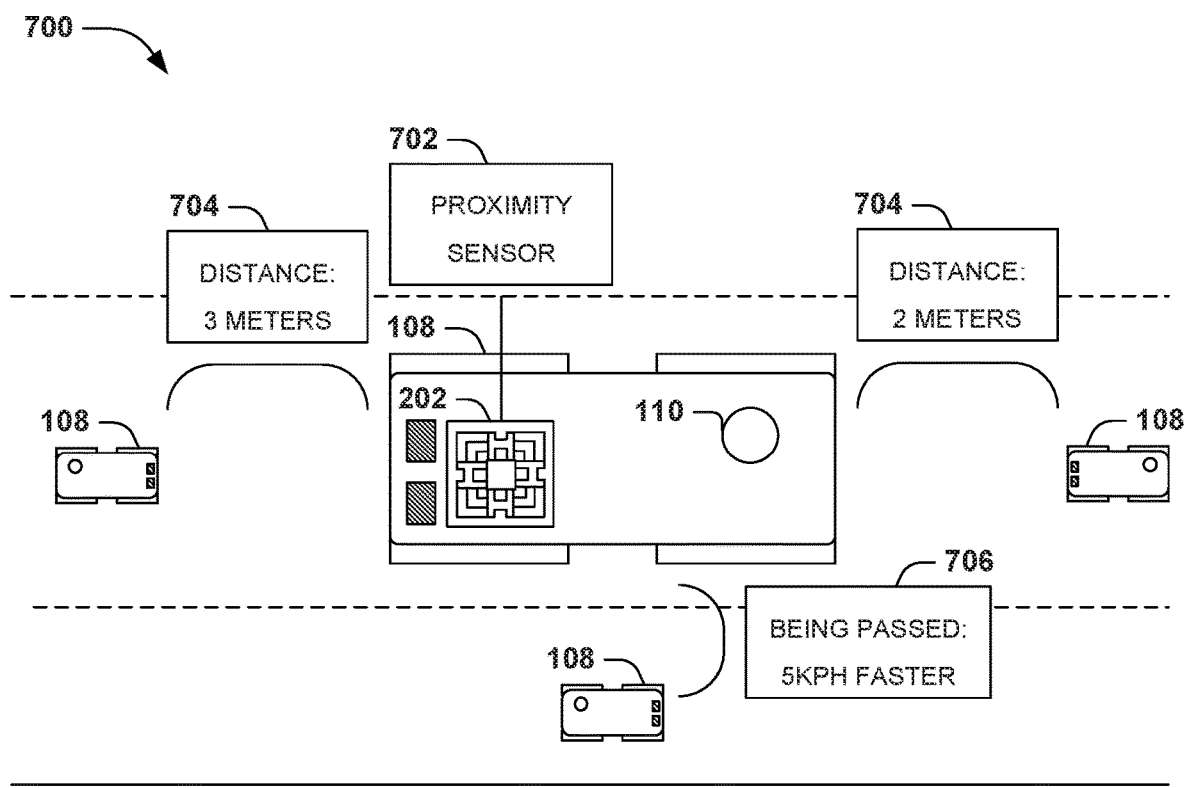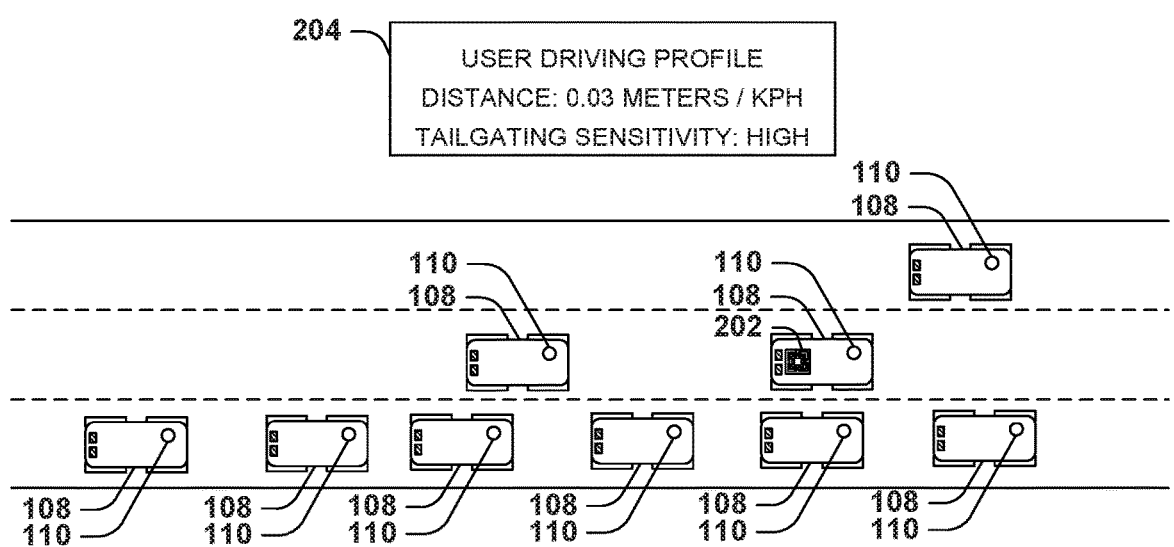
FIG. 7

800 →

DRIVING PROFILES

| 110 | 802 USER | 804 | 206 USER DRIVING BEHAVIOR | | | 206 |
|---|---|---|---|---|---|---|
| | USER MOOD | USER CONTEXT | 106 SPEED 106 | | BRAKING DISTANCE | |
| | | | SUNNY | RAIN | SUNNY | RAIN |
| 1 | RELAXED | TOURING | SLOW | SLOW | MEDIUM | LONG |
| | HAPPY | ON TIME | MEDIUM | SLOW | MEDIUM | LONG |
| | ANXIOUS | LATE | FAST | FAST | SHORT | MEDIUM |

| 110 USER | 902 MODEL |
|---|---|
| 1 | CAUTIOUS |
| 2 | AVERAGE |
| 3 | AGGRESSIVE |

USER BEHAVIOR DRIVING MODELS

| 902 MODEL | 208 206 USER DRIVING BEHAVIOR 206 | | | |
|---|---|---|---|---|
| | 106 SPEED 106 | | BRAKING DISTANCE | |
| | SUNNY | RAIN | SUNNY | RAIN |
| CAUTIOUS | SLOW | SLOW | LONG | LONG |
| AVERAGE | MEDIUM | SLOW | MEDIUM | MEDIUM |
| AGGRESSIVE | FAST | MEDIUM | SHORT | MEDIUM |

FIG. 9

PERSONALIZATION OF AUTOMATED VEHICLE CONTROL

BACKGROUND

Within the field of computing, many scenarios involve an automation of control of at least one aspect of a vehicle. For example, current automobile technology often includes automated speed control to maintain a steady speed. When a user requests a controller to maintain a steady speed of a vehicle, the controller may operate a fuel inlet to adjust the engine speed and the achieved speed of the vehicle, but the degree of adjustment involved in maintaining a current speed may fluctuate based on other factors, such as the incline of the road surface. The controller may therefore use feedback mechanisms to compare the current vehicle speed and the selected vehicle speed, and to select the appropriate degree of fuel adjustment. Other properties that are currently subject to automation include a maintained distance from a leading vehicle; parallel parking assistance; the selection of lights, including regular or high beams; and the use and speed of windshield wipers. Such automation may also includes aspects within the vehicle, such as controlling the volume level of radio in relation to the noise level outside of the vehicle.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One disadvantage that often arises within vehicle control scenarios involves differences between the parameters of automated control and the driving behavior of the user. As a first example, the precision with which a vehicle seeks to achieve a requested speed may vary; e.g., an aggressive control mechanism may make frequent adjustments of the engine rate toward the requested speed to attain higher precision, but with reduced travel comfort. Conversely, a relaxed control mechanism may more gradually adjust the engine rate toward the requested speed to provide a smoother ride, but with slower responsiveness to changing conditions. These variations may be noticeable to the driver and passengers, who may have different preferences as to the tradeoff between precision and travel comfort. As a second example, control mechanisms may utilize speed control and braking to maintain a safe distance from a leading vehicle, but different drivers may have differing opinions as to a "safe" distance. A fixed control mechanism may appear to be overcautious to some drivers who prefer to maintain a shorter braking distance, and may appear to be unsafe to other drivers who prefer to maintain a longer braking distance. This discrepancy may discourage some users from using the automated control features of the vehicle, while other users may vacillate between using automated control and manually operating the vehicle (e.g., selecting automated speed control, but also frequently manipulating the accelerator and brake of the vehicle to achieve driving that is in line with the user's driving behaviors).

Presented herein are techniques for personalizing the automated control of a vehicle based on the driving behavior of the user. In accordance with these techniques, while a user is operating a vehicle in a driving context (e.g., during the day, at night, or during bad weather), a device may monitor respective driving features of the vehicle during operation in the driving context (e.g., detecting vehicle speed, rates of acceleration and braking, and braking distance maintained with respect to leading vehicles) in order to detect the user driving behaviors of the user in the driving context (e.g., whether the user typically drives over or at the speed limit; whether the user typically accelerates quickly or slowly from stoplights; whether the user accelerates or decelerates quickly or slowly in order to adjust the speed of the vehicle toward a change in a speed limit; and whether the user typically maintains a long or short braking distance with respect to leading vehicles). When requested to control a driving feature of the vehicle in a driving context (e.g., by the user, or upon detecting a condition where autonomous control is to be spontaneously invoked, such as an emergency braking system), a controller may identify the user driving behavior of the user in the driving context, and may operate the driving feature of the vehicle according to the identified user driving behavior. In this manner, the automated control of the vehicle may be personalized to the user driving behaviors of one or more users.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DESCRIPTION OF THE DRAWINGS

FIG. 2 is an illustration of an example scenario featuring an identification of the user driving behaviors of users of a vehicle in various contexts, and the automated control of driving features of the vehicle reflecting the user driving behaviors, in accordance with the techniques presented herein.

FIG. 7 is an illustration of an example scenario featuring a method of detecting the driving features of the driving profile of a user in accordance with the techniques presented herein.

FIG. 8 is an illustration of an example scenario featuring techniques for further personalizing the driving features of a vehicle in accordance with the techniques presented herein.

FIG. 9 is an illustration of an example scenario featuring techniques for classifying users according to a driving behavior type in accordance with the techniques presented herein.

DETAILED DESCRIPTION

Figure 1:
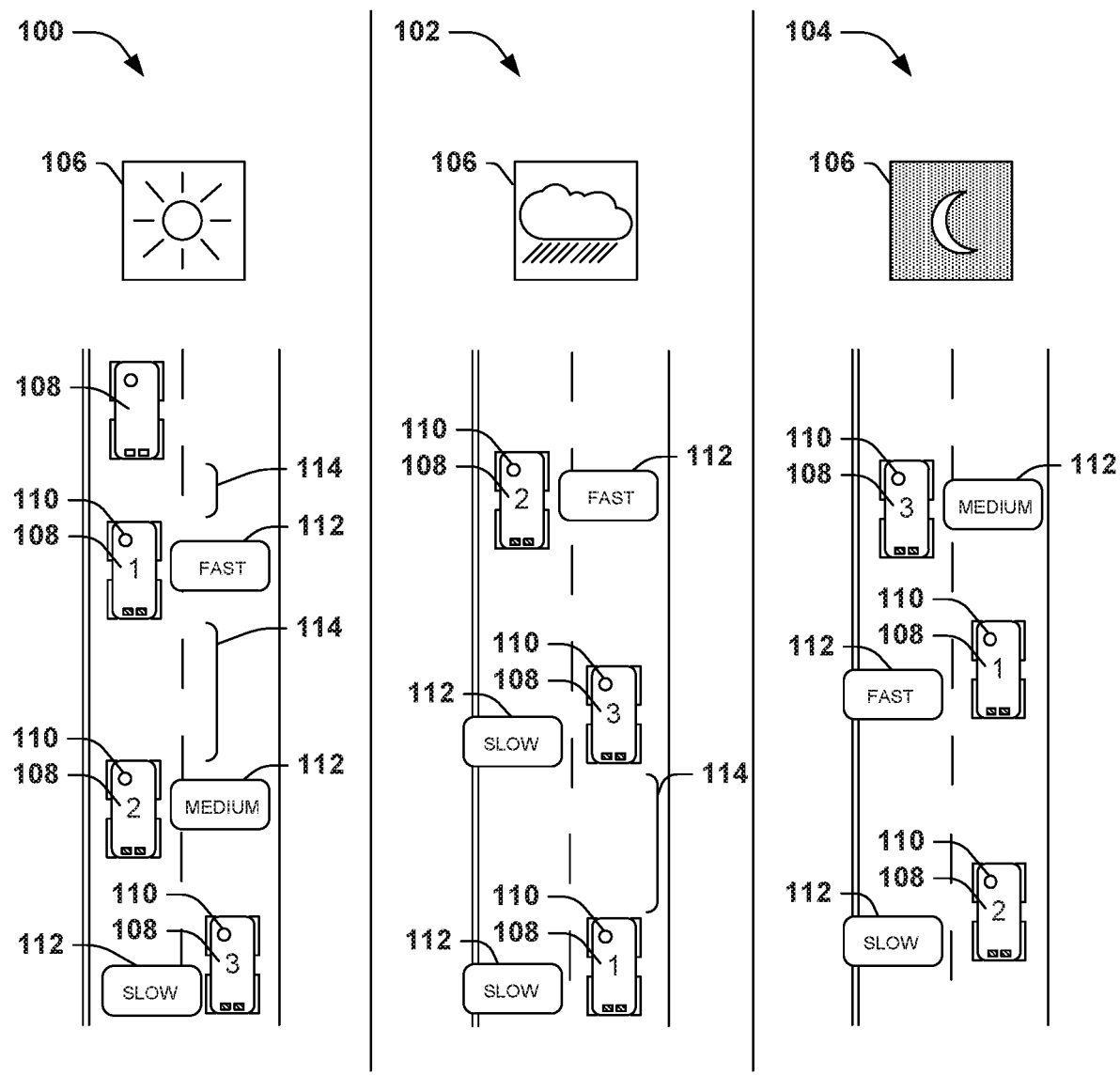
FIG. 1 is an illustration of an example scenario featuring variable user driving behaviors of users in various driving contexts.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A. Introduction

In the field of vehicles, many techniques provide for automated control of various driving features of a vehicle on behalf of a user operating the vehicle. As a first example, many automobiles are equipped with speed control that is usable to maintain a steady speed, thus freeing the driver from constantly adjusting the accelerator to account for minor variances in the speed of the vehicle. Such speed control mechanisms often utilize feedback, which compares a current speed of the vehicle with a selected or target speed, and then adjusts the fuel rate provided to the engine to alter the engine speed and, over time, achieve the target speed, while also compensating for minor variance, such as changes in the incline of the road surface. Other examples of automated vehicle control include (e.g.) the braking distance maintained with respect to a leading vehicle; automated parallel parking; the use and mode selection for headlights, such as automatically selecting high beams, regular beams, or fog lamps; and the use and speed of windshield wipers in response to weather conditions. Automated control may also extend to the interior of a vehicle, such as automatically adjusting climate control features to achieve a target interior temperature, and adjusting the sound of a sound system in order to overcome varying levels of ambient noise. However, it may be appreciated that different users exhibit different driving behaviors, and may be sensitive to the operation of the vehicle in a manner that conflicts with the preferred driving behaviors of the user.

FIG. 1 presents an illustration of various example scenarios 100 depicting the variance of users 110 in operating the driving features of vehicles 108. In a first example scenario 100 arising in a first driving context 106 (e.g., daytime driving on a particular span of roadway in good weather conditions and light traffic), users 110 may operate vehicles 108 on the roadway according to different driving preferences. For example, a first user 110 may operate a first vehicle 108 at a fast speed 112 while maintaining a short braking distance 114 with respect to a leading vehicle 108, while a second user 110 operates a second vehicle 108 at a medium speed 112 and with a longer braking distance 114, and a third user 110 operates a third vehicle 108 at a slow speed 112 and with very large braking distance 114 (e.g., preferring to select a lane that is not occupied by other nearby vehicles 108). However, the user driving behaviors of the users 110 may change in different driving context 106. In a second example scenario 102 involving inclement daytime weather, the first user 110 (e.g., who may be sensitive to the dangers of hydroplaning) may operate the first vehicle 108 at a slow speed 112, while the second user 110 (e.g., who may be experienced and confident while driving in inclement weather) may operate at a faster relative speed 12 than in the daytime driving context 106, while the third user 110 continues to operate at a slow speed 112. In a third example scenario 104 during a third driving context 106 (e.g., nighttime), the first user 110 may again drive at a fast speed 108, but the second user 110 (e.g., who may have poor night vision) may instead drive at a slow speed 112, while the third user 110 (e.g., who may have strong night vision) may driving at a higher speed 112 relative to other driving conditions 106. Similar variations may occur with respect to other driving features (e.g., the first user may prefer to maintain a short braking distance 114 in the first driving context 106, but may prefer to maintain a much longer braking distance 114 in the second driving context 106, while the preferences of the second and third users 110 may not significantly change in different driving contexts 106).

Such variance in driving behavior among users 110 may diminish the satisfaction achieved by automated vehicle control, due to perceived discrepancies between the parameters of automated driving control and the user driving behaviors of the user 110. Moreover, because different users 110 may prefer to operate a vehicle in a driving context in a different manner, it may be difficult to design an automated controller that is suitable to a wide range of users 110. For example, it may be possible to select control parameters that reflect a typical driving style among a body of drivers or according to accepted safety standards, but these designs may still be unsatisfying to the particular user 110 who has requested the use of the automated control of the vehicle 108. Such dissatisfaction may result in diminished or intermittent use of the automated control feature, or conflicts between the user driving behaviors of the user and the automated controller. For example, a driver may select automated speed control, but may frequently manipulate the accelerator and brake in order to adapt the selected speed to changing conditions and/or preferences. Such conflicting control may diminish the perceived effectiveness of the automated controller, and in some cases may lead to dangerous conditions in the operation of the vehicle.

B. Presented Techniques

Presented herein are techniques for automatically controlling a vehicle 108 in a manner that is personalized to the user driving behaviors of the user 110 who is operating the vehicle 108. In accordance with these techniques, while the user 110 operates the vehicle 108 in a driving context 106, a device may monitor one or more driving features of the vehicle 108 (e.g., speed, acceleration, braking, turning, gear selection, and/or the use of accessories such as headlights, turn signals, windshield wipers, climate control, and sound systems) in order to detect one or more user driving behaviors of the user 110 in the driving context 106. These user driving behaviors may vary from direct user input to the driving features of the vehicle 108 (e.g., the user's maximum rates of acceleration and deceleration) to higher-level determinations (e.g., a comparison of the speed of the vehicle 108 with a posted speed limit). When requested to control one or more driving features of the vehicle 108 in a particular driving context 106, a device may identify one or more user driving behaviors of the user 110 in the driving context 106, and may control the driving features of the vehicle 108 according to the user driving behaviors of the user 110. As a lower-level example, when requested to maintain a selected speed, the device may utilize acceleration and braking rates that are typical of the user 110 (e.g., accelerating and braking aggressively when an aggressive driver is operating the vehicle 108, and accelerating and braking more gradually when a relaxed driver is operating the vehicle 108). As a higher-level example, while the user 110 is controlling the speed of the vehicle 108, the device may compare the speed of the vehicle 108 with the posted speed limit in order to determine the user's typical preference for driving over, at, or under the speed limit; and when requested to maintain a steady speed, the device may continuously adapt the target speed with respect to the current speed limit in order to reflect the speed preferences of the user 110. These and many other control parameters may be selected and utilized to personalize the automated control of the vehicle 108 to the preferences of the user 110.

FIG. 2 presents an illustration of an example scenario featuring an application of the techniques presented herein. In this example scenario, at a first time point 200, while various users 110 are operating vehicles 108 in a driving context, a device 202 on board each vehicle 108 may monitor one or more user driving behaviors of various driving features of the vehicle 108, such as the speed 112 and braking distance 114 with respect to a leading vehicle 108. For example, a first user 110 may operate a first vehicle 108 may be driven at a fast speed 114 with a short braking distance 114; a second user 110 may operate a second vehicle 108 may be driven at a medium speed 114 with a medium braking distance 114; and a third user 110 may operate a first vehicle 108 may be driven at a slow speed 114 with a large braking distance 114. Based on this monitoring, the device 202 may generate a set of user driving profiles 204, each indicating the user driving behaviors 208 of various driving features 206 of the vehicle 108. At a second time point 210, when the user 110 operating the vehicle 108 initiates a request 212 for the device 202 to control a driving feature 206 of the vehicle 108 such as speed, the device 202 may identify 214 the user 110, and select 216 at least one user driving behavior 216 of the user 110 in the driving context 206 of the vehicle 108 (e.g., by comparing current conditions, such as the time of day and weather conditions, with the conditions recorded in the user driving profile 204 of the user 110, and selecting the user driving behavior 208 of the user 110 for the driving feature 206 in the user driving profile 204). The device 202 may then control the vehicle 108 according to the user driving behavior 208 of the user 110. In this manner, the automated control of the vehicle 108 may be personalized based on the user driving behaviors 208 of the user 110, thus facilitating the satisfaction of the user 110 with the automated control of the vehicle 108 in accordance with the techniques presented herein.

C. Technical Effects

The techniques presented herein may enable a variety of technical effects in the scenarios provided herein.

As a first such example, the techniques provided herein may enable autonomous control of a vehicle 108 in a manner that is more consistent with the driving style of the user 110. While many control systems may be applied to operate a particular vehicle 108, some options and tradeoffs in the details and parameters of such control systems may be available, such that a variety of control systems are acceptably safe and performant. However, a user 110 who does not like the options and tradeoffs selected for a particular vehicle control system may be disinclined to engage it to operate the vehicle 108. For example, a control system that selects a particular driving speed may be deemed too slow for the driving behaviors 208 of a first user 110, and yet too fast for the driving behaviors 208 of a second user 110, and as a result, one or both users 110 may choose not to use the vehicle control system.

As a second such example, the techniques provided herein may enable an autonomous control system for a vehicle 108 to adapt to circumstances that may reflect the driving behaviors 208 of the user 110, but that may have escaped the attention of the user 110 during manual operation of the vehicle 108. For example, the user 110 may often choose to drive slowly during winter conditions, and an autonomous driving system may, accordingly, control the vehicle 108 at a reduced speed when winter conditions develop. However, in some circumstances, the user 110 may fail to recognize that road conditions may be slippery (e.g., in conditions where "black ice" is likely to form, or on suspended bridges that are more susceptible to freezing). A user 110 might fail to appreciate such conditions during operation of the vehicle 108, and may therefore fail to apply his or her own driving behaviors 208 for slower driving during icy conditions. By contrast, an autonomous vehicle control system may detect such conditions even in conditions where the user 110 may not, and may control the vehicle 108 in a manner reflecting the driving behaviors 208 of the user 110 even more consistently than the user 110 may be capable of maintaining. Similarly, if the driving behaviors 208 of a first user 110 are to be utilized even while the vehicle 108 is operated by a second user 110 (e.g., an owner of the vehicle 108 may specify a set of driving behaviors 208 to be utilized while controlling the vehicle 108 on behalf of another driver), the first user's driving behaviors 208 may be consistently applied to the control of the vehicle 108 even where the second user's driving behaviors 208 differ.

As a third such example, the techniques provided herein may enable an autonomous control system for a vehicle 108 to adapt automatically to the driving behaviors 208 of a user 110. While some driving systems may present an adjustable parameter, the adaptation of the current control of the vehicle 108 to the driving behaviors 208 of a particular user 110 may involve frequent adjustment of the control system (e.g., a control system may permit the user 110 to select a current driving speed to be maintained for the vehicle 108, but as the user's driving behaviors 208 change according to different circumstances, the user 110 may have to frequently adjust the selected speed). In addition to presenting an irritation to the user 110, such frequent adjustment may impose a safety risk by distracting the user 110 from the operation of the vehicle 108. Alternatively, if the user 110 fails to select an adjustment when circumstances change, the vehicle 108 may be operated in an unsafe manner (e.g., the safe speed limit for a particular road may be reduced, but the user 110 may forget to reduce a steady driving speed that has been selected for a cruise control system, and the vehicle 108). A vehicle control system that adjusts the control of the vehicle 108 to reflect the driving behaviors 208 of the user 110 in various circumstances may entail less attention and/or adjustment from the user 110, and may therefore reduce safety risks of non-adaptive control systems. The driving behaviors 208 of the user 110 may also be utilized during autonomous control of the vehicle 108, e.g., in circumstances where an autonomous control system controls the vehicle through the entirety of transit from an origin to a destination, and/or where the vehicle invokes autonomous control, e.g., as part of an emergency braking system responsive to the detection of an obstacle ahead. These and other technical effects may be achievable by driving control systems configured in accordance with the techniques presented herein.

D. Example Embodiments

Figure 3:
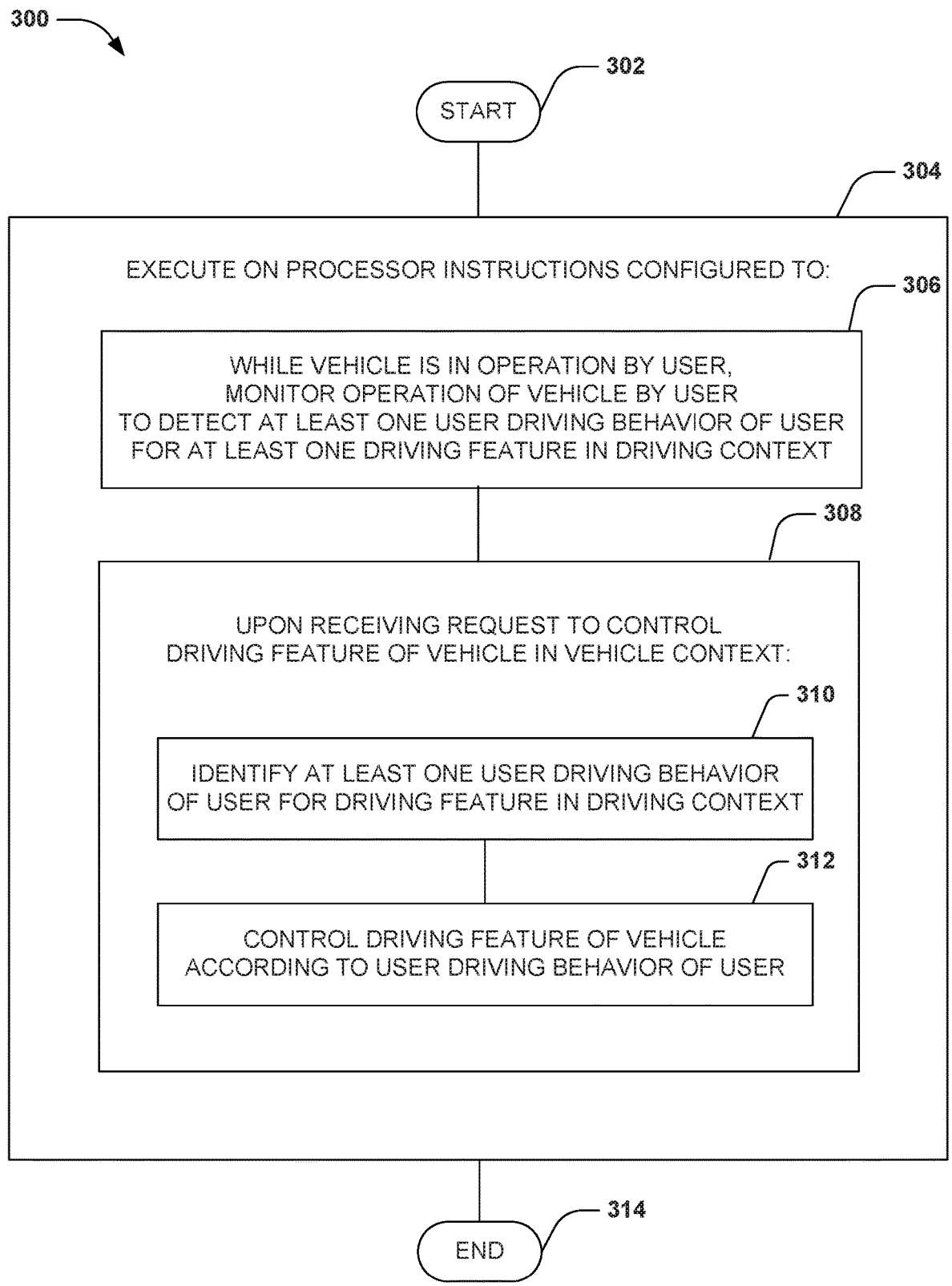
FIG. 3 is an illustration of an example method of controlling a vehicle operated by a user in accordance with the techniques presented herein.

FIG. 3 presents a first example embodiment of the techniques presented herein, illustrated as an example method 300 of controlling a vehicle 108 operated by a user 110. The example method 300 may be implemented on a device having a processor and having access to one or more driving features 208 of the vehicle 108. The example method 300 may be implemented, e.g., as a set of instructions stored in a memory component of a device (e.g., a memory circuit, a platter of a hard disk drive, a solid-state memory component, or a magnetic or optical disc) that, when executed by the processor of the device, cause the device to perform the techniques presented herein. The example method 300 begins at 302 and involves executing 304 the instructions on the processor. Specifically, the instructions are configured to, while the vehicle 110 is in operation by a user 108, monitor 306 the operation of the vehicle 110 by the user 108 to detect at least one user driving behavior 208 of the user 110 for at least one driving feature 206 of the vehicle 110 in a driving context 106. The instructions are also configured to, upon receiving 308 a request 212 to control a driving feature 208 of the vehicle 108 in a driving context 106, identify 310 at least one user driving behavior 208 of the user 110 for the driving feature 206 of the vehicle 108 in the driving context 106, and control 312 the driving feature 206 of the vehicle 108 according to the at least one user driving behavior 208 of the user 110. In this manner, the example method 300 achieves the automated control of the driving features 206 of the vehicle 108 in a manner that is personalized to the user driving behaviors 208 of the user 110, and so ends at 314.

Figure 4:
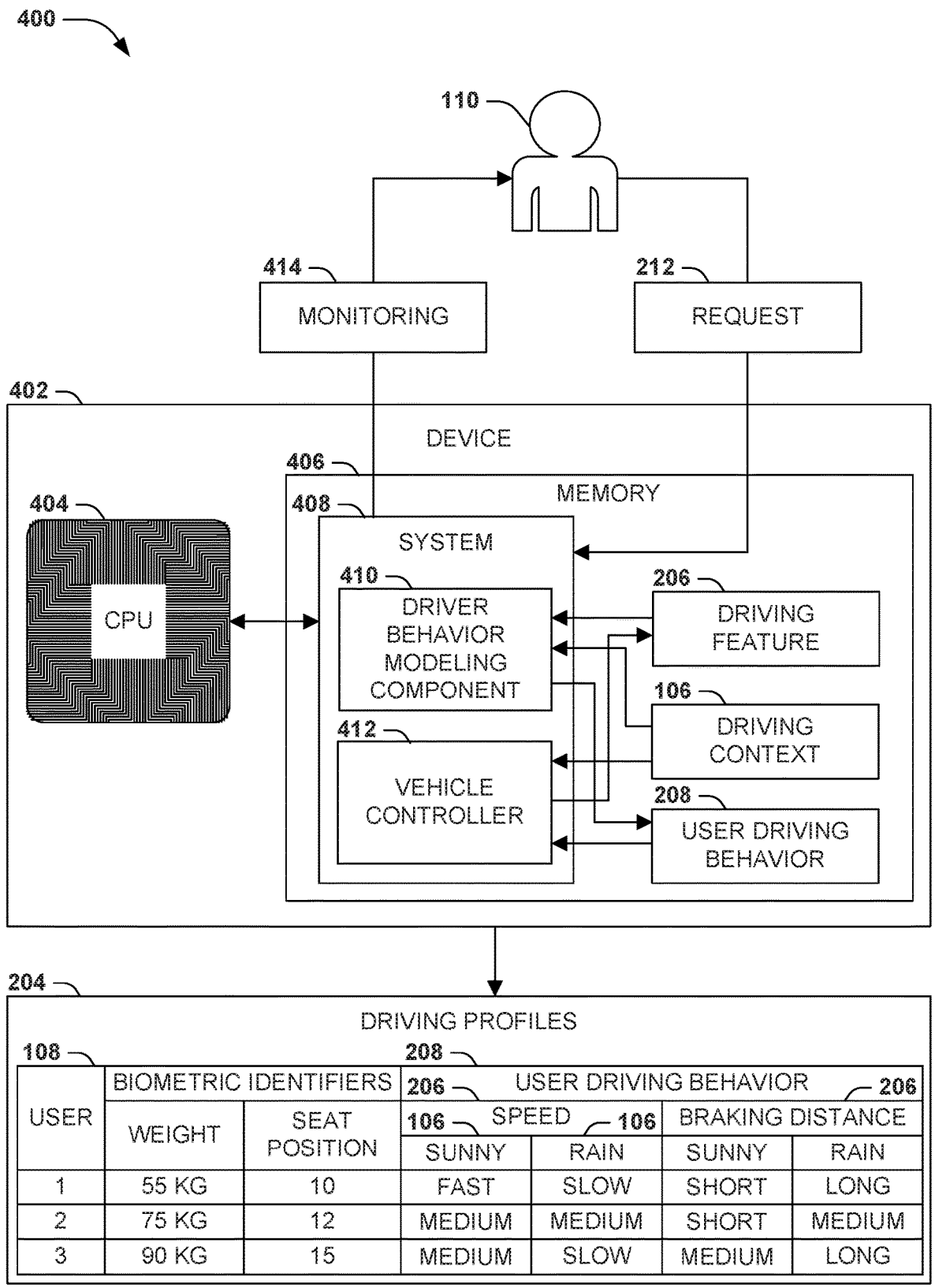
FIG. 4 is a component block diagram of an example system for controlling a vehicle operated by a user in accordance with the techniques presented herein.

FIG. 4 presents an illustration of an example scenario 400 featuring a second example embodiment of the techniques presented herein, illustrated as an example system 408 for controlling a vehicle 108 operated by a user 108. The example system 408 may be implemented, e.g., on a device 402 having a processor 404 and a memory 406. Respective components of the example system 408 may be implemented, e.g., as a set of instructions stored in a memory 406 of the device 402 and executable on the processor 404 of the device 402, such that the interoperation of the components causes the device 402 to operate according to the techniques presented herein. The example system 408 comprises a driving behavior modeler 410 that, while the vehicle 108 is in operation by the user 110, monitors the operation of the vehicle 108 by the user 110 to detect at least one user driving behavior 208 of the user 110 for at least one driving feature 206 of the vehicle 108 in a driving context 106. The example system 408 also comprises a vehicle controller 412 that, upon receiving a request 212 to control a driving feature 206 of the vehicle 108 in a driving context 106, identifies at least one user driving behavior 208 of the user 110 for the driving feature 206 of the vehicle 108 in the driving context 106; and controls the driving feature 206 of the vehicle 108 according to the user driving behavior 208 of the user 110. In this manner, the example system 408 achieves the automated control of the driving features 206 of the vehicle 108 in a manner that is personalized to the user driving behaviors 208 of the user 110.

Still another embodiment involves a computer-readable medium comprising processor-executable instructions configured to apply the techniques presented herein. Such computer-readable media may include, e.g., computer-readable storage media involving a tangible device, such as a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a CD-R, DVD-R, or floppy disc), encoding a set of computer-readable instructions that, when executed by a processor of a device, cause the device to implement the techniques presented herein. Such computer-readable media may also include (as a class of technologies that are distinct from computer-readable storage media) various types of communications media, such as a signal that may be propagated through various physical phenomena (e.g., an electromagnetic signal, a sound wave signal, or an optical signal) and in various wired scenarios (e.g., via an Ethernet or fiber optic cable) and/or wireless scenarios (e.g., a wireless local area network (WLAN) such as WiFi, a personal area network (PAN) such as Bluetooth, or a cellular or radio network), and which encodes a set of computer-readable instructions that, when executed by a processor of a device, cause the device to implement the techniques presented herein.

Figure 5:
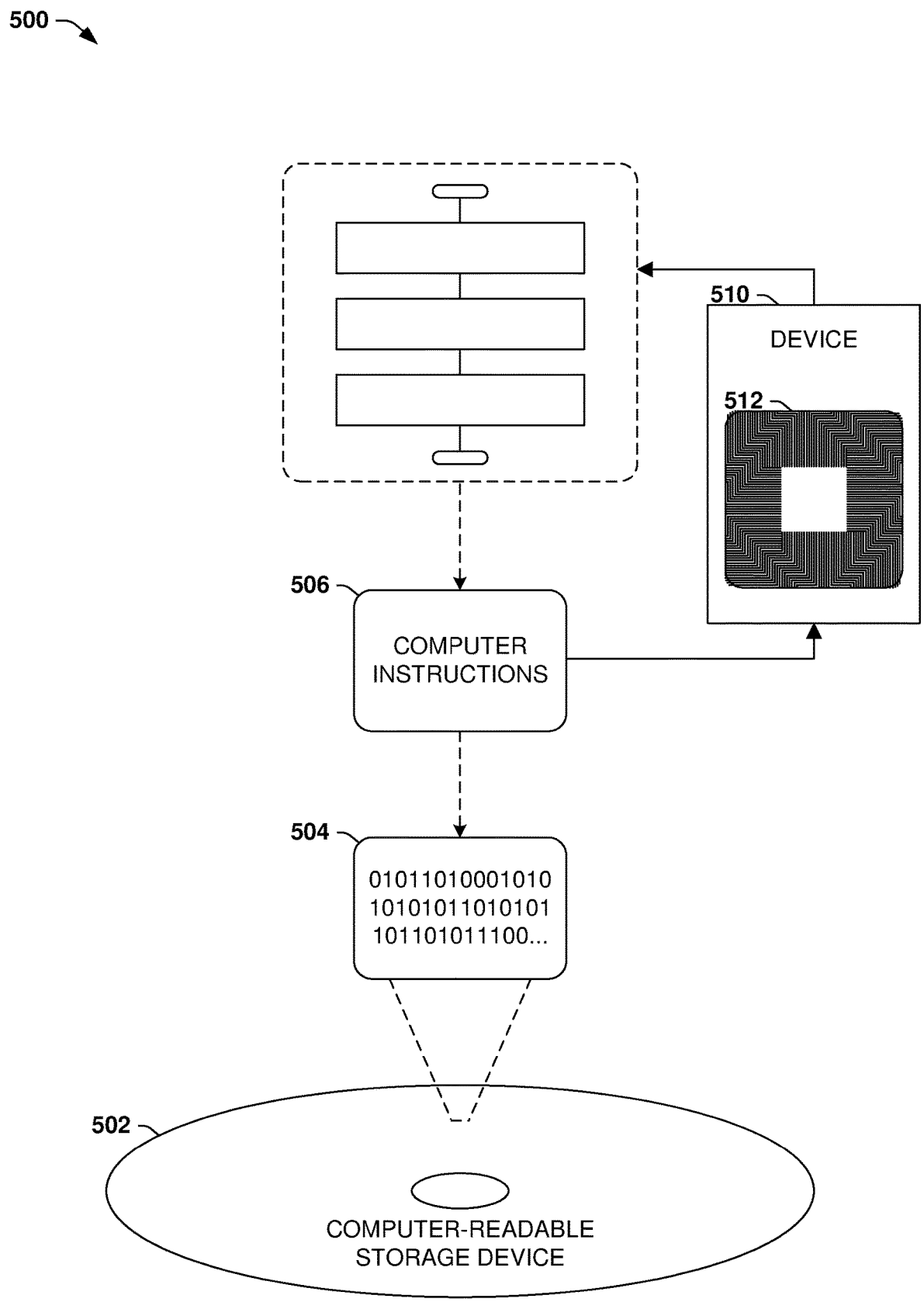
FIG. 5 is an illustration of an example computer-readable medium comprising processor-executable instructions configured to embody one or more of the provisions set forth herein.

An example computer-readable medium that may be devised in these ways is illustrated in FIG. 5, wherein the implementation 500 comprises a computer-readable medium 502 (e.g., a CD-R, DVD-R, or a platter of a hard disk drive), on which is encoded computer-readable data 504. This computer-readable data 504 in turn comprises a set of computer instructions 506 configured to operate according to the principles set forth herein. In a first such embodiment, the processor-executable instructions 506 may be configured to, when executed by a processor 512 of a device 510, cause the device 510 to control one or more driving features 206 of a vehicle 108 consistently with the user driving behaviors 208 of a user 110, such as the example method 300 of FIG. 3. In a second such embodiment, the processor-executable instructions 506 may be configured to implement a system for controlling one or more driving features 206 of a vehicle 108 consistently with the user driving behaviors 208 of a user 110, such as the example system 408 of FIG. 4. Some embodiments of this computer-readable medium may comprise a nontransitory computer-readable storage medium (e.g., a hard disk drive, an optical disc, or a flash memory device) that is configured to store processor-executable instructions configured in this manner. Many such computer-readable media may be devised by those of ordinary skill in the art that are configured to operate in accordance with the techniques presented herein.

Figure 6:
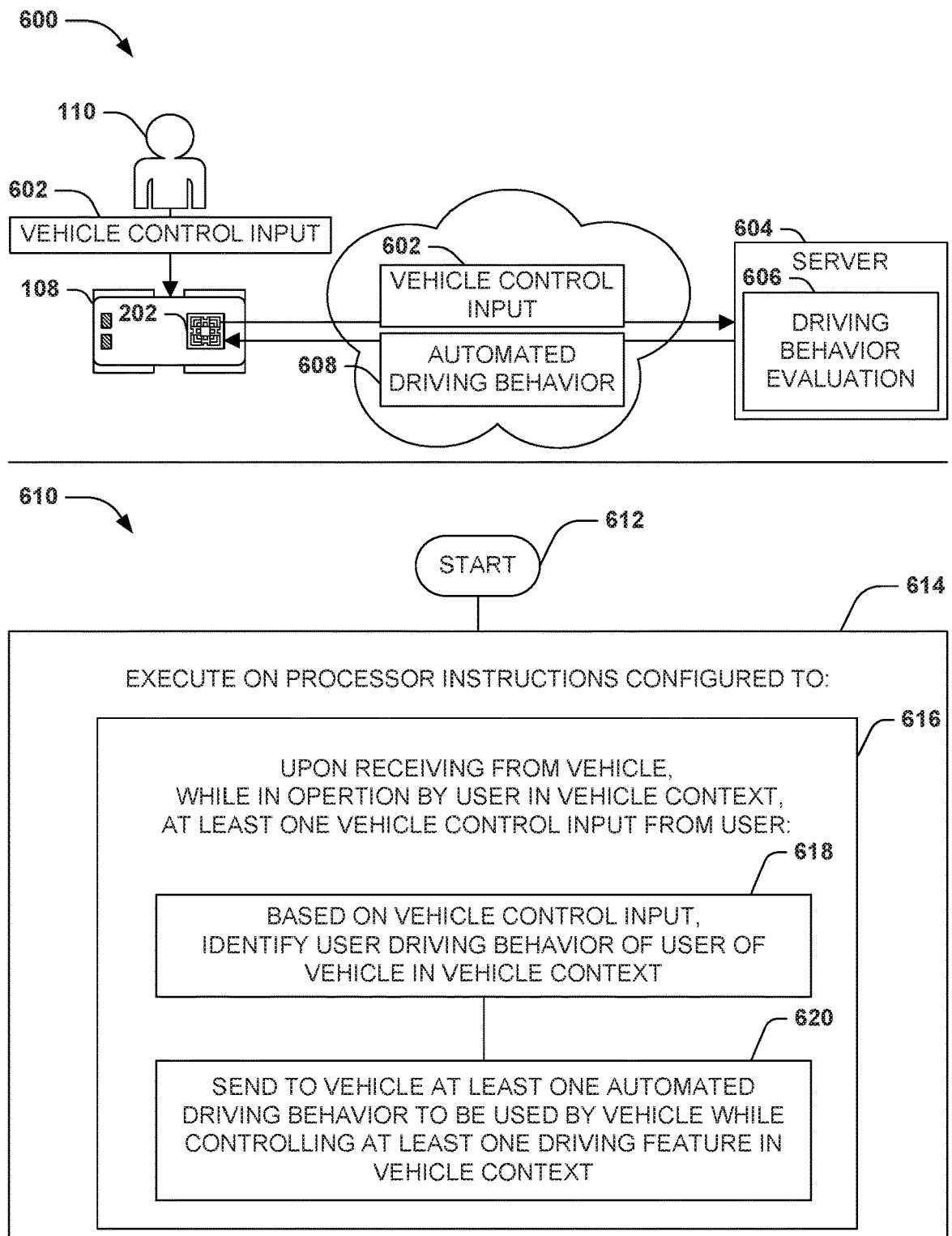
FIG. 6 is an illustration of an example scenario featuring a second example method of controlling vehicles according to user driving behaviors in accordance with the techniques presented herein.

Some embodiments of the techniques presented herein may involve an interoperation of devices in order to achieve the techniques presented herein. FIG. 6 presents an illustration of an example scenario 600 featuring a distributed technique involving a server 604 intercommunicating with a device 202 in order to provide automated control of a vehicle 108 operated by a user 110. In this example scenario 600, the device 202 detects vehicle control input 602 provided by the user 110 (e.g., input to the accelerator, brake, gearshift, and steering wheel) while operating the vehicle 108 in a driving context 604, and sends the vehicle control input 602 to the server 604 (e.g., through a wireless uplink with a communications network such as the internet). The server 604 performs a driving behavior evaluation 604, e.g., by performing an example method 610 beginning at 612 and involving executing 614 instructions on a processor of the server 604. In particular, the instructions are configured to, upon receiving from the device 202 at least one vehicle control input 602, identify a user driving behavior 604 of the user 110 with respect to the operation of the vehicle 108 in the driving context 106 based on the vehicle control input 602 (e.g., determining that the user 110 prefers fast acceleration, moderate braking speeds, and a long braking distance with respect to leading vehicles 108). The instructions may further send to the vehicle 108 and the device 202 at least one automated driving behavior 608 to be used by the device 202 while controlling at least one driving feature 206 of the vehicle 108 (e.g., a logic for controlling the driving features 206 of the vehicle 108 in accordance with the user driving behaviors 208 of the user 110). In this manner, the instructions executed by the server 604 may facilitate the device 202 in controlling the vehicle 108 in a manner personalized to the user driving behaviors 208 of the user 110, and so the example method 610 ends at 622.

E. Variable Aspects

The techniques discussed herein may be devised with variations in many aspects, and some variations may present additional advantages and/or reduce disadvantages with respect to other variations of these and other techniques. Moreover, some variations may be implemented in combination, and some combinations may feature additional advantages and/or reduced disadvantages through synergistic cooperation. The variations may be incorporated in various embodiments (e.g., the example method 300 of FIG. 3; the example system 408 of FIG. 4; the example computer-readable storage device 502 of FIG. 5; and the example method 610 of FIG. 6) to confer individual and/or synergistic advantages upon such embodiments.

E1. Scenarios

A first aspect that may vary among embodiments of these techniques relates to the scenarios wherein such techniques may be utilized.

As a first example of this first aspect, the techniques presented herein may be used with many types of vehicles 108, including automobiles, motorcycles, trucks, buses, watercraft, aircraft, drones, and spacecraft. Such vehicles may be controlled by one or more humans, may be autonomous, or may involve a combination thereof, such as an autonomous automobile that can also be controlled by a human.

As a second example of this first aspect, the techniques presented herein may be used to automate the control many types of types of driving features 206 of the vehicle 108, such as an accelerator, or throttle, brake, gear selector, steering wheel, tiller, or yolk. The driving features 206 may also include vehicle accessories, including interior and exterior lighting; windshield wipers; cleaning, anti-fogging, and/or de-icing controls; climate controls; sound systems; and communication with other vehicles 108 and individuals.

As a third example of this first aspect, the techniques presented herein may be used to control the driving features 206 of the vehicle 108 according to various user driving behaviors 208 of the user 108. As a first example, when requested to maintain a selected speed, the device may utilize acceleration and braking rates that are typical of the user 110 (e.g., accelerating and braking aggressively when an aggressive driver is operating the vehicle 108, and accelerating and braking more gradually when a relaxed driver is operating the vehicle 108). As a second example, while the user 110 is controlling the speed of the vehicle 108, the device may compare the speed of the vehicle 108 with the posted speed limit in order to determine the user's typical driving behaviors 208 for driving over, at, or under the speed limit; and when requested to maintain a steady speed, the device may continuously adapt the target speed with respect to the current speed limit in order to reflect the speed driving behaviors 208 of the user 110. Other examples of the types of use driving behaviors 208 that may be detected and utilized during automated control of the driving features 206 include the braking rates of the user 110 (e.g., whether the user prefers stopping over short distances or more gradually over longer distances); the speed and/or turning profile of the vehicle 108 while traversing curves; the altitude and/or attitude of an airborne vehicle 108; a maintained distance of the vehicle 108 with respect to at least one other vehicle 108; the driving behaviors 208 of the user 110 to yield to other vehicles 108; a lane change frequency of the vehicle 108 between at least two lanes; a refuelling threshold of the vehicle 108 (e.g., the threshold at which the vehicle 108 recommends seeking a fuel replenishing source); a routing criterion of a route of the vehicle 108 (e.g., whether a navigation system chooses routes that are faster, more efficient, more reliable, less expensive, and/or more scenic); and parallel parking techniques.

As a fourth example of this first aspect, the techniques presented herein may be used to determine the user driving behaviors 206 of the user 110 while operating the vehicle 108 in a variety of driving contexts 106, including the time of day; sunny, overcast, foggy, rainy, snowing, and/or freezing weather conditions; a vehicle causeway type context (e.g., an unpaved local road, a residential side street, a main roadway, or a highway); a traffic congestion context (e.g., the volume of traffic in the vicinity of the vehicle 108); a vehicle speed of at least one other vehicle 108 operating near the vehicle 108 (e.g., if the vehicle 108 is passing, being passed by, or keeping pace with other vehicles 108); the route of the vehicle 108 (e.g., a short local route, a longer cross-city route, or a long-distance route between cities); and a vehicle condition context (e.g., the maintenance condition and/or cargo contents of the vehicle 108); and a vehicle passenger context (e.g., the number and identities of other passengers aboard the vehicle 108).

As a fourth example of this first aspect, the techniques presented herein may be invoked in a variety of circumstances. As a first such example, the user 110 may initiate a request for autonomous control of the vehicle 108, such as by engaging a cruise control feature of the vehicle 108. As a second such example, the vehicle 108 may be completely autonomous, and may conduct the entirety of transit from an origin to a destination according to the user driving behaviors 208 of the user 110. As a third such example, the vehicle 108 may detect an opportunity or contingency to utilize an autonomous driving feature, such as an emergency braking feature that may be utilized to avoid an accident, and may apply the autonomous driving feature in accordance with to the user driving behaviors 208 of the user 110. These and other variations may arise regarding the scenarios within which the techniques may be advantageously utilized.

E2. Driving Contexts and User Driving Behaviors

A second aspect that may vary among embodiments of these techniques involves the detection the user driving behaviors of the driving features 206 of the vehicle 108, and the driving context 106 which the user 110 is operating the vehicle 108.

As a first variation of this second aspect, the driving context 106 of the vehicle 108 may be detected in various ways. As a first such example, the driving context 106 may be detected by a device 202 on board the vehicle 108 through communication with various sensors, e.g., a clock that provides the time of day, and ambient sensors that detect the temperature, light level, and moisture. As a second such example, the driving context 106 may be inferred from the driving features 206 of the vehicle, e.g., inferring from an activation of antilock brakes that a road is wet or icy. As a third such example, nearby vehicles 108 traveling in a local region may intercommunicate to determine the driving conditions; e.g., a first vehicle 108 that detects a slippery road surface may broadcast this driving context 206 to other vehicles 108 in the area. As a fourth such example, the driving context 106 may be received as a set of driving context descriptors from a driving context service (e.g., a service accessible over a communications network that informs the device 202 on board the vehicle 108 of the driving conditions in the area, such as the ambient weather and road surface conditions).

As a second variation of this second aspect, a device 202 providing automated control of a particular vehicle 108 may distinguish and track the user driving behaviors 208 for more than one user 110 who may operate the vehicle 108 at different times, and may personalize the automated control of the vehicle 108 based on the particular set of user driving behaviors 208 of the user 110 operating the vehicle 108 during the automated control. For example, among at least two users 110, the device may, upon detecting that a user 110 is operating the vehicle 108, determine an identity of the user 110. As one such example, as illustrated in the example scenario 400 of FIG. 4, the identity of the current user 110 may be detected according to various biometric identifiers, such as a detected weight of the user 110, and a detected seat position (indicative of leg length, and therefore height). Other techniques for detecting the identity of the user 110 may include identification credentials provided by the current user 110 (e.g., detecting a driver's license carried by the user 110); facial recognition software; a vehicle control input 602 initiated by the current user 110 for the vehicle 108 in a current travel context; and a user driving behavior of the current user 110 for a driving feature 206 of the vehicle 108 (e.g., determining the identity of the user 110 according to a distinctive driving style of the user 110). Upon detecting a user driving behavior 208, the device 202 may store the user driving behavior 208 associated with the identity of the user 110. Thereafter, the device 202 may fulfill a request to control a driving feature 206 of the vehicle 108 by identifying the identity of current user 110 of the vehicle 108; identifying the user driving behaviors 206 associated with the identity of the current user 110; and controlling the driving features 206 according to the selected user driving behaviors 206.

FIG. 7 presents an illustration of an example scenario 700 featuring a third variation of this second aspect, wherein a device 202 may control the vehicle 108 according to the driving behaviors 208 of a user 110. In this example scenario 700, the device 202 features a proximity sensor 702 that detects a proximity of the vehicle 108 to other vehicles 108 in via a number of techniques, such as visual evaluation of camera data; ranging data gathered by sonar, radar, and/or lidar detection; and/or electronic communication with other vehicles 108. Using such techniques, the proximity sensor 702 detects the manner in which the user 110 controls the vehicle 108 in view of its proximity to other vehicles 108, such as a distance 704 between the vehicle 108 of the user 110 and another vehicle 108 that is ahead of and/or behind the vehicle 108 of the user 110; the relative speeds of the vehicles 108 ahead of and/or behind the user 110; and/or the rates of acceleration, braking, turning, and/or swerving by the user 110 and the drivers of the other vehicles 108. The proximity sensor 702 may also detect information about vehicles 108 in other lanes of the road, such as the relative or absolute speeds of vehicles 108 in adjacent lanes, and/or whether or not such vehicles 108 are passing 706 and/or are being passed by the vehicle 108. Based on such information, the device 202 may evaluate how the user 110 operates the vehicle 108 in proximity to other vehicles 108, and may adjust the user driving profile 204 (e.g., how closely the user 110 chooses to drive with respect to another vehicle 108; how the user 110 reacts to close driving or "tailgating" by a following vehicle 108, such as when the user 110 chooses to change lanes and allow the following vehicle 108 to pass; and whether the user 110 is sensitive to driving next to another vehicle 108 in scenarios with narrow lanes). Accordingly, when autonomously controlling the vehicle 108, the device 202 may adjust such control according to the proximity sensitivities of the user 110.

FIG. 8 presents an illustration of an example scenario 800 featuring a fourth variation of this second aspect, wherein the vehicle 108 may be operated by the user 110 in one of at least two user contexts. For example, the mood 802 of the user 110 (e.g., the user 110 may drive differently when relaxed, happy, and anxious), and/or as the user context 804 of the user 110 varies (e.g., when the user 110 is touring an area; when the user 110 is traveling to a meeting and is on time; and when the user 110 is traveling to a meeting and is running late). The device 202 may detect the user context of the user 110, e.g., if it is specified by the user 110; through a biometric measurement of the user 110, such as heart rate, respiration rate, or blood pressure; through an interior vehicle control request initiated by the user 110, such as the type of music or navigation requested by the user 110; through vehicle control input 602 initiated by the user 110 for the vehicle 108 in a current travel context 106; and/or a user driving behavior of the user 110 for a driving feature 206 of the vehicle 108 in a driving context 106 (e.g., the current driving style of the user 110). In accordance with this variation, a device 202 may store respective detected user driving behaviors 206 associated with the current user context of the user 110, and upon receiving a request to automate control of a driving feature 206 of the vehicle 108, may identify a current user context of the user 110, and control the driving feature 206 according to the user driving behaviors 208 that are associated with the current user context of the user 110.

As a third variation of this second aspect, the user driving behaviors 208 detected for the user 110 and/or utilized during automated control of a driving feature 206 may be associated with various user interests indicated by the user 110. For example, the user 110 may specify a time conserving user interest; a time predictability promoting user interest (e.g., a driving style that promotes a consistent prediction of an arrival time); a toll reduction user interest; a fuel economizing user interest; a vehicle maintenance reducing user interest; an emission reducing user interest; a driving safety promoting user interest; and a smooth driving experience promoting user interest.

FIG. 9 presents an illustration of a fourth variation of this second aspect, wherein the user driving behaviors 208 are identified according to respective user driving behavior models. In this example scenario 900, a device 202 and/or server 604 may store a set of user behavior driving models 902. The user behavior driving models 902 may, e.g., reflect driving styles such as a cautious driving model, an average driving model, and an aggressive driving model; demographics, such as elderly drivers, middle-age drivers, and young drivers; and/or an experience level, such as a professional driver, a casual driver, and an inexperienced driver.

Each user behavior driving model 902 may also specify a set of user driving behaviors 208 that are characteristic of users 110 associated with the user behavior driving model 902. Accordingly, a device 202 or server 604 may compare the user driving behaviors 902 of respective users 110 with the available user driving behavior models 902 in order to classify the user 110 as one of several available user driving types (e.g., comparing the user driving behavior of the user to the driving behavior prototype models to classify the user according to a driving behavior type), and such classification may be aggregated across large bodies of users 110 (e.g., using Bayesian classification techniques). For example, a device 202 or server 604 may comprise at least two driving behavior prototype models that respectively describe a user driving behavior of users 110 of a driving behavior type. The automated control of driving features 206 of the vehicle may therefore be based on the user driving behaviors 208 that are characteristic of the user behavior driving model 902 of the user 110, even if the device 202 or server 604 has not previously monitored the operation of the vehicle 108 by the user 110 in the current driving context 106. For example, even if the user 110 has never driven in snow conditions, the automated control of the vehicle 108 in snow conditions may be personalized to the user driving behaviors 208 of the user by choosing the user driving behaviors 208 that are characteristic of the user behavior driving model 902 of the user 110.

As a fifth variation of this second aspect, the automated control of the driving features 206 of the vehicle 110 may vary based on vehicle control input 602 provided by the user 110 during the automated control of the vehicle 110. As a first such example, an automated controller may select a first rate of acceleration, but the user 110 may apply a heavier rate of acceleration in conflict with the selected rate. As a second such example, the automated controller may select an acceleration of the vehicle 108, but the user 110 may apply the brakes of the vehicle 108 in conflict with the automatically selected acceleration. A device 202 may adapt to the conflicting vehicle control input 602 of the user 110 in various ways. As a first such example, upon detecting a user vehicle control input 602 that is initiated by the user 110 and that conflicts with control of the driving feature 206 of the vehicle 108, the device 202 may control the vehicle 110 according to the vehicle control input 602 instead of the user driving behavior 208 of the user 110 (e.g., ceding control to the user 110 as a control override). As a second such example, the device 202 may adjust the user driving behavior 208 of the user 110 for the driving feature 206 of the vehicle 108 in the driving context 106 (e.g., more finely tuning the user driving behaviors 208 to the driving behaviors 208 of the user 110).

As a sixth variation of this second aspect, a device 202 or server 604 may describe for the user 110 the user driving behavior 208 of the user 110 for at least one driving feature 206 of the vehicle 108 in at least one driving context 106. For example, the device 202 may provide to the user 110 a description of the user's detected driving style, possibly along with tips for improving the safety, comfort, or efficiency of the user's driving style. These and other variations in the user context and the automated control of driving features 206 may be included in implementations of the techniques presented herein.

F. Computing Environment

Figure 10:
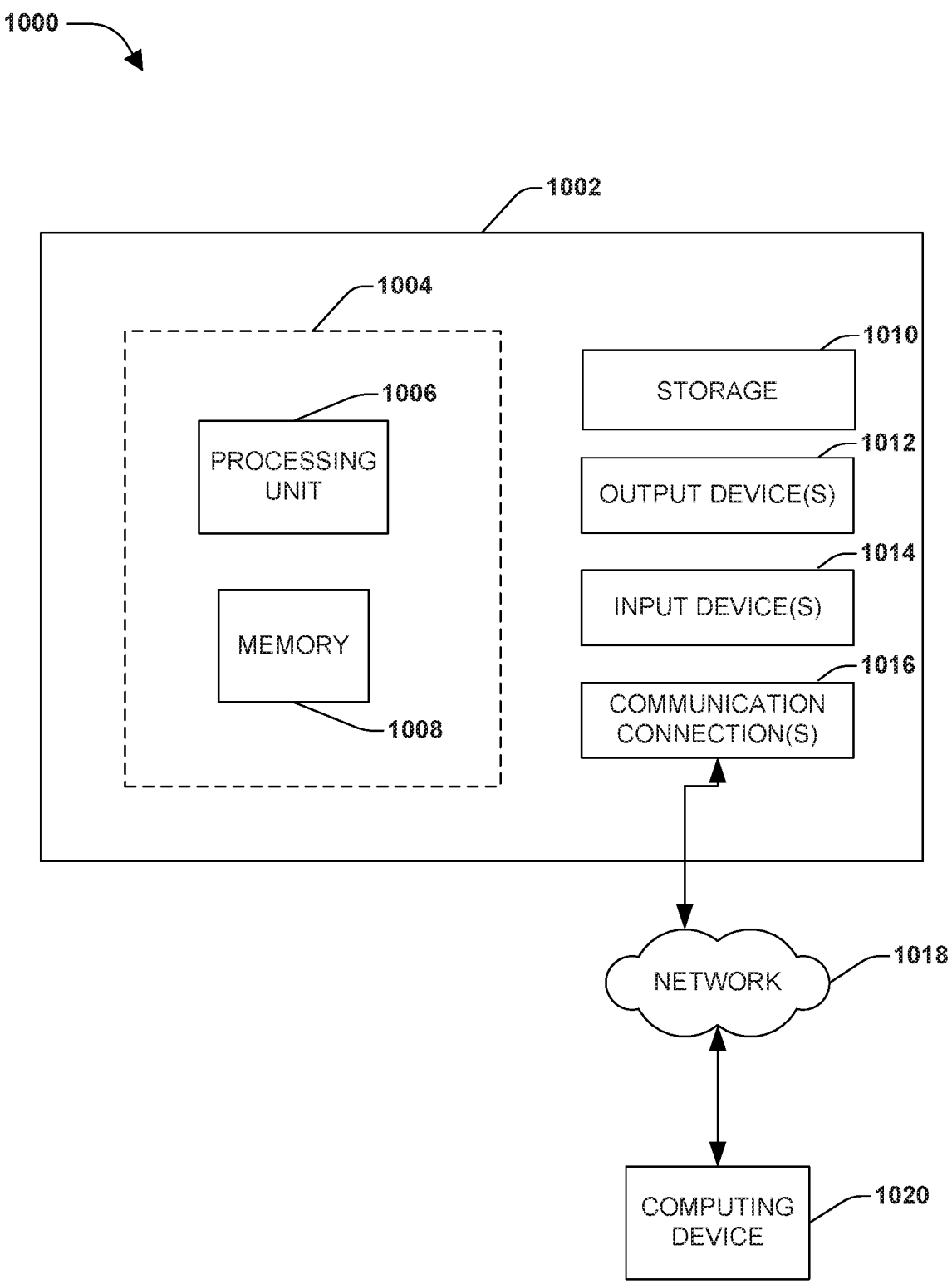
FIG. 10 illustrates an example computing environment wherein one or more of the provisions set forth herein may be implemented.

FIG. 10 and the following discussion provide a brief, general description of a suitable computing environment to implement embodiments of one or more of the provisions set forth herein. The operating environment of FIG. 10 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 10 illustrates an example of a system 1000 comprising a computing device 1002 configured to implement one or more embodiments provided herein. In one configuration, computing device 1002 includes at least one processing unit 1006 and memory 1008. Depending on the exact configuration and type of computing device, memory 1008 may be volatile (such as RAM, for example), non-volatile (such as ROM, flash memory, etc., for example) or some combination of the two. This configuration is illustrated in FIG. 10 by dashed line 1004.

In other embodiments, device 1002 may include additional features and/or functionality. For example, device 1002 may also include additional storage (e.g., removable and/or non-removable) including, but not limited to, magnetic storage, optical storage, and the like. Such additional storage is illustrated in FIG. 10 by storage 1010. In one embodiment, computer readable instructions to implement one or more embodiments provided herein may be in storage 1010. Storage 1010 may also store other computer readable instructions to implement an operating system, an application program, and the like. Computer readable instructions may be loaded in memory 1008 for execution by processing unit 1006, for example.

The term "computer readable media" as used herein includes computer storage media. Computer storage media includes volatile and nonvolatile, removable and non-removable media implemented in any method or technology for storage of information such as computer readable instructions or other data. Memory 1008 and storage 1010 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 1002. Any such computer storage media may be part of device 1002.

Device 1002 may also include communication connection(s) 1016 that allows device 1002 to communicate with other devices. Communication connection(s) 1016 may include, but is not limited to, a modem, a Network Interface Card (NIC), an integrated network interface, a radio frequency transmitter/receiver, an infrared port, a USB connection, or other interfaces for connecting computing device 1002 to other computing devices. Communication connection(s) 1016 may include a wired connection or a wireless connection. Communication connection(s) 1016 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 1002 may include input device(s) 1014 such as keyboard, mouse, pen, voice input device, touch input device, infrared cameras, video input devices, and/or any other input device. Output device(s) 1012 such as one or more displays, speakers, printers, and/or any other output device may also be included in device 1002. Input device(s) 1014 and output device(s) 1012 may be connected to device 1002 via a wired connection, wireless connection, or any combination thereof. In one embodiment, an input device or an output device from another computing device may be used as input device(s) 1014 or output device(s) 1012 for computing device 1002.

Components of computing device 1002 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 1002 may be interconnected by a network. For example, memory 1008 may be comprised of multiple physical memory units located in different physical locations interconnected by a network.

Those skilled in the art will realize that storage devices utilized to store computer readable instructions may be distributed across a network. For example, a computing device 1020 accessible via network 1018 may store computer readable instructions to implement one or more embodiments provided herein. Computing device 1002 may access computing device 1020 and download a part or all of the computer readable instructions for execution. Alternatively, computing device 1002 may download pieces of the computer readable instructions, as needed, or some instructions may be executed at computing device 1002 and some at computing device 1020.

G. Usage of Terms

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "example" is used herein to mean serving as an example, instance, or illustration. Any aspect or design described herein as "example" is not necessarily to be construed as advantageous over other aspects or designs. Rather, use of the word example is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method of configuring a device to control a vehicle operated by a first user, the method comprising:
executing on the device instructions configured to:
while the vehicle is in operation by the first user:
monitor the operation of the vehicle by the first user to detect at least one user driving behavior of the first user for at least one driving feature of the vehicle in a first driving context to develop a first portion of a first driving profile for the first user; and
monitor the operation of the vehicle by the first user to detect at least one user driving behavior of the first user for at least one driving feature of the vehicle in a second driving context to develop a second portion of the first driving profile for the first user; and
upon receiving a request to control at least one driving feature of the vehicle in a driving context:
determine whether the vehicle is being controlled by the first user or a second user different than the first user;
determine whether the driving context is the first driving context or the second driving context;
when the driving context is the first driving context and the vehicle is being controlled by the first user:
identify the at least one user driving behavior of the first user for the at least one driving feature of the vehicle in the first driving context based upon the first driving profile; and
control the at least one driving feature of the vehicle according to the at least one user driving behavior of the first user for the at least one driving feature of the vehicle in the first driving context;
when the driving context is the second driving context and the vehicle is being controlled by the first user:
identify the at least one user driving behavior of the first user for the at least one driving feature of the vehicle in the second driving context based upon the first driving profile; and
control the at least one driving feature of the vehicle according to the at least one user driving behavior of the first user for the at least one driving feature of the vehicle in the second driving context, wherein the at least one driving feature is controlled differently based upon whether the driving context is the first driving context or the second driving context;
when the vehicle is being controlled by the second user, use a second driving profile for the second user to control one or more driving features of the vehicle when the second driving profile for the second user exists; and
when the vehicle is being controlled by the second user and no driving profile exists for the second user:
compare driving behaviors of the second user to driving behavior models created based upon driving behaviors of a plurality of users to identify a driving behavior model for the second user; and
use the driving behavior model to control the at least one driving feature of the vehicle.

2. The method of claim 1, wherein the at least one driving feature is selected from a driving feature set comprising:
a velocity of the vehicle in a driving context;
an acceleration of the vehicle in a driving context;
a maintained distance of the vehicle with respect to at least one other vehicle in a driving context;
a lane change frequency of the vehicle between at least two lanes in a driving context;
a refueling threshold of the vehicle in a driving context; and
a routing criterion of a route of the vehicle in a driving context.

3. The method of claim 1, wherein the driving context is selected from a driving context set comprising:
a vehicle causeway type context;
a vehicle type context;
a vehicle condition context;
a traffic congestion context;
a vehicle speed of at least one other vehicle operating near the vehicle;
a weather context;
a time of day context; and
a vehicle passenger context.

4. The method of claim 1, wherein the instructions are further configured to detect the driving context by receiving at least one driving context descriptor from a driving context service.

5. The method of claim 1, wherein:
the instructions are further configured to:
upon detecting a user operating the vehicle, determine an identity of the user; and
upon detecting a user driving behavior of the user of the vehicle, store the user driving behavior associated with the identity of the user.

6. The method of claim 5, wherein the determining whether the vehicle is being controlled by the first user or a second user different than the first user comprises:
identifying an identity of a current user according to a user identifying feature selected from a user identifying feature set comprising:
an identification credential provided by the current user;
a biometric measurement of the current user;
a vehicle control input initiated by the current user for the vehicle in a current travel context; and
a user driving behavior of the current user for a driving feature of the vehicle in a driving context.

7. The method of claim 1, wherein:
the vehicle is operated by the first user in one of at least two user contexts;
the instructions are further configured to:
upon detecting the first user operating the vehicle, determine a user context of the first user in the first driving context; and
upon detecting at least one user driving behavior of the first user of the vehicle, store the at least one user driving behavior associated with the user context of the first user;
the determining whether the driving context is the first driving context or the second driving context comprises identifying a current user context of the first user; and
the instructions are further configured to:
when the driving context is the first driving context and the vehicle is being controlled by the first user:

identify the at least one user driving behavior associated with the current user context of the first user for the at least one driving feature of the vehicle in the first driving context.

8. The method of claim 7, wherein the identifying the current user context of the first user comprises:
identifying the current user context of the first user according to a user context identifying feature set comprising:
a user context specified by the first user;
a biometric identifier of the first user;
an interior vehicle control request initiated by the first user;
a vehicle control input initiated by the first user for the vehicle in a current travel context; and
a user driving behavior of the first user for a driving feature of the vehicle in a driving context.

9. The method of claim 1, wherein, when the driving context is the first driving context and the vehicle is being controlled by the first user, the controlling the at least one driving feature further comprises:
controlling the at least one driving feature of the vehicle according to the at least one user driving behavior of the first user and at least one user interest indicated by the first user.

10. The method of claim 9, wherein the at least one user interest of the first user is selected from a user interest set comprising:
a time conserving user interest;
a time predictability promoting user interest;
a toll reduction user interest;
a fuel economizing user interest;
a vehicle maintenance reducing user interest;
an emission reducing user interest;
a driving safety promoting user interest; and
a smooth driving experience promoting user interest.

11. The method of claim 1, wherein the detecting the at least one user driving behavior comprises:
comparing at least one vehicle control input initiated by the first user with at least one user driving behavior model; and
determining the at least one user driving behavior of the first user according to the at least one user driving behavior model.

12. The method of claim 11, wherein:
the device comprises at least two driving behavior prototype models respectively describing a user driving behavior of users of a driving behavior type; and
the determining the at least one user driving behavior further comprises:
comparing the at least one user driving behavior of the first user to the at least two driving behavior prototype models to classify the first user according to a driving behavior type; and
determining the at least one user driving behavior of the first user according to the driving behavior prototype model of the driving behavior type of the first user.

13. The method of claim 1, wherein, when the driving context is the first driving context and the vehicle is being controlled by the first user, the identifying the at least one user driving behavior comprises:
sending at least one vehicle control input initiated by the first user in the first driving context to a user driving behavior evaluation service.

14. The method of claim 13, wherein the instructions are further configured to receive from the user driving behavior evaluation service at least one automated driving behavior resembling the at least one user driving behavior of the first user.

15. The method of claim 1, wherein the instructions are further configured to, when the driving context is the first driving context and the vehicle is being controlled by the first user, upon detecting a user vehicle control input initiated by the first user and conflicting with controlling one or more of the at least one driving feature of the vehicle according to the at least one user driving behavior of the first user, adjust the at least one user driving behavior of the first user for the at least one driving feature of the vehicle in the first driving context.

16. The method of claim 1, wherein the instructions are further configured to, when the driving context is the first driving context and the vehicle is being controlled by the first user, describe for the first user the at least one user driving behavior of the first user for at least one driving feature of the vehicle in the first driving context.

17. The method of claim 1, wherein the first portion of the first driving profile for the first user describes how the user manually controls one or more operational parameters of the vehicle while driving in the first driving context.

18. A system comprising:
a processor; and
memory comprising instructions that when executed by the processor cause operations for configuring a device to control a vehicle operated by a first user, the operations comprising:
monitoring the operation of the vehicle by the first user to detect at least one user driving behavior of the first user for at least one driving feature of the vehicle in a first driving context to develop a first portion of a first driving profile for the first user;
monitoring the operation of the vehicle by the first user to detect at least one user driving behavior of the first user for at least one driving feature of the vehicle in a second driving context to develop a second portion of the first driving profile for the first user; and
upon receiving a request to control at least one driving feature of the vehicle in a driving context:
determining whether the driving context is the first driving context or the second driving context;
when the driving context is the first driving context and the vehicle is being controlled by the first user:
identifying the at least one user driving behavior of the first user for the at least one driving feature of the vehicle in the first driving context based upon the first driving profile; and
controlling the at least one driving feature of the vehicle according to the at least one user driving behavior of the first user for the at least one driving feature of the vehicle in the first driving context;
when the driving context is the second driving context and the vehicle is being controlled by the first user:
identifying the at least one user driving behavior of the first user for the at least one driving feature of the vehicle in the second driving context based upon the first driving profile; and
controlling the at least one driving feature of the vehicle according to the at least one user driving behavior of the first user for the at least one driving feature of the vehicle in the second driving context, wherein the at least one driving feature is controlled differently based upon whether the driving context is the first driving context or the second driving context; and when the driving context does not match any, known driving context for the first user:

comparing driving behaviors of the first user to driving behavior models created based upon driving behaviors of a plurality of users to identify a driving behavior model for the first user in the driving context; and using the driving behavior model to control the at least one driving feature of the vehicle.

19. The system of claim 18, wherein the operations further comprise detecting the driving context by receiving at least one driving context descriptor from a driving context service.

20. A method of configuring a device to control a vehicle operated by a first user, the method comprising:

executing on the device instructions configured to:

while the vehicle is in operation by the first user and a second entity is present in the vehicle:

monitor the operation of the vehicle by the first user to detect at least one user driving behavior of the first user for at least one driving feature of the vehicle to develop a first portion of a driving profile for the first user;

while the vehicle is in operation by the first user and the second entity is not present in the vehicle:

monitor the operation of the vehicle by the first user to detect at least one user driving behavior of the first user for at least one driving feature of the vehicle to develop a second portion of the driving profile for the first user; and upon receiving a request to control at least one driving feature of the vehicle:

determine whether the vehicle is being controlled by the first user and whether the second entity is present in the vehicle;

when the vehicle is being controlled by the first user and the second entity is present in the vehicle:

identify the at least one user driving behavior of the first user for the at least one driving feature of the vehicle based upon the first portion of the driving profile; and control the at least one driving feature of the vehicle according the at least one user driving behavior of the first user associated with the first portion of the driving profile; and when the vehicle is being controlled by the first user and the second entity is not present in the vehicle:

identify at least one second user driving behavior of the first user for the at least one driving feature of the vehicle based upon the second portion of the driving profile; and control the at least one driving feature of the vehicle according the at least one user driving behavior of the first user associated with the second portion of the driving profile.

* * * * *